United States Patent
Obler et al.

(10) Patent No.: US 12,138,100 B1
(45) Date of Patent: Nov. 12, 2024

(54) METHOD FOR OPERATING AN X-RAY IMAGING SYSTEM, METHOD FOR GENERATING A DATABASE, CONTROL SYSTEM, X-RAY IMAGING SYSTEM, CONTROL FACILITY, COMPUTER PROGRAM AND ELECTRONICALLY READABLE DATA STORGE MEDIUM

(71) Applicant: Siemens Healthineers AG, Forchheim (DE)

(72) Inventors: Richard Obler, Erlangen (DE); Philipp Bernhardt, Forchheim (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/661,118

(22) Filed: May 10, 2024

(30) Foreign Application Priority Data

May 10, 2023 (DE) .................. 10 2023 204 333.5

(51) Int. Cl.
*G06T 7/80* (2017.01)
*A61B 6/00* (2006.01)

(52) U.S. Cl.
CPC ............... *A61B 6/54* (2013.01); *A61B 6/481* (2013.01)

(58) Field of Classification Search
CPC ....... G06T 2207/00; G06T 2207/10072; G06T 2207/10116; G06T 2207/10141; G06T 2207/20; G06T 2207/20182; G06T 2207/10144; G06T 2207/20172; G06T 2207/10081; G06T 5/50; G06T 5/70;
(Continued)

(56) References Cited

U.S. PATENT DOCUMENTS

| | | | |
|---|---|---|---|
| 2003/0097057 A1* | 5/2003 | Oshio | A61B 5/055 600/410 |
| 2005/0286681 A1 | 12/2005 | Bernhardt | |
| 2020/0085402 A1 | 3/2020 | Obler | |

FOREIGN PATENT DOCUMENTS

| | | |
|---|---|---|
| DE | 102004030833 A1 | 1/2006 |
| DE | 102018215958 A1 | 3/2020 |

OTHER PUBLICATIONS

Decision to Grant for German App. No. 10 2023 204 333.5 mailed Feb. 6, 2024, with English translation.
(Continued)

*Primary Examiner* — Don K Wong
(74) *Attorney, Agent, or Firm* — Lempia Summerfield Katz LLC

(57) ABSTRACT

A method for operating an X-ray imaging system includes outputting first X-ray beams onto an X-ray detector by an X-ray source for acquisition of a first X-ray capture of an object under examination. The object under examination is arranged between the X-ray source and the X-ray detector and is passed through by the first X-ray beams. The X-ray detector acquires an entry dose of the first X-ray beams after passage through the object under examination. A parameter value of at least one parameter for output of second X-ray beams by the X-ray source for acquisition of a second X-ray capture of the object under examination is ascertained by a control system. The parameter value is ascertained by the control system according to a specified ascertainment method as a function of a foreground substance of a foreground object, a background substance of a background object, and the entry dose.

11 Claims, 4 Drawing Sheets

(58) Field of Classification Search
CPC ......... G06T 5/94; A61B 6/5258; A61B 6/545; A61B 6/542
See application file for complete search history.

(56) References Cited

OTHER PUBLICATIONS

German Office Action for German App. No. 10 2023 204 333.5 mailed Dec. 22, 2023, with English translation.

* cited by examiner

METHOD FOR OPERATING AN X-RAY IMAGING SYSTEM, METHOD FOR GENERATING A DATABASE, CONTROL SYSTEM, X-RAY IMAGING SYSTEM, CONTROL FACILITY, COMPUTER PROGRAM AND ELECTRONICALLY READABLE DATA STORGE MEDIUM

This application claims the benefit of German Patent Application No. DE 10 2023 204 333.5, filed on May 10, 2023, which is hereby incorporated by reference in its entirety.

BACKGROUND

The present embodiments relate to a method for operating an X-ray imaging system, a method for generating a database, a control system, an X-ray imaging system, a control facility, a computer program, and an electronically readable data storage medium.

According to the current prior art, medical X-ray imaging systems may include a point-shaped X-ray source for outputting X-rays toward an object under examination that is to be examined. The object under examination may, for example, be a patient. The X-rays pass through the object under examination, and some are absorbed by the object under examination. A linear and/or two-dimensional spatially-resolving detector capable of acquiring the X-rays is arranged behind the object under examination.

The X-ray beams image a cross-section of the object under examination. As a function of the absorption of the X-ray beams along their respective courses, locally acquired X-ray beams have different intensities that are brought about by the anatomy.

According to the current prior art, medical X-ray systems are very often equipped with automatic exposure controllers. In these systems, an actual dose at the detector input is measured during irradiation of an object under examination. This value is then compared with a nominal dose. Based on a difference between the actual dose and the nominal dose, irradiation parameters are adapted for further irradiation of the object under examination. The irradiation parameters include, for example, a tube voltage, a tube current, an exposure time, and/or a prefiltering of the X-ray beams for the next examination. The irradiation parameters are adapted for the next measurement such that the nominal dose at the detector input may be achieved in the next measurement.

The dynamics are distinctly higher in more recent detectors. According to the current prior art, it is thus no longer necessary to keep the dose at the detector input constant and the dose may be configured at any time to the requirements of image quality and patient dose.

Nevertheless, different substances respond differently to the energy of the X-ray spectrum because an absorption of X-ray beams by the substances is dependent on the energy of the X-ray beams.

In order to obtain a better depiction in an X-ray capture of a foreground object that includes a foreground substance, irradiation parameter values are set so as to maximize a contrast-to-noise ratio relating to a difference between a second signal intensity value in the X-ray capture of a second X-ray beam that has passed through the background object and the foreground object in comparison with a first signal intensity value in the X-ray capture of a first X-ray beam of the X-ray beams that has only passed through the background object in an object under examination.

Although the current prior art offers various solutions for optimizing the contrast of the foreground object to be depicted in the X-ray capture for different foreground substances, of which the foreground object may consist, the background substance in which the foreground object to be depicted is arranged is always the same. The background substance is a specified average mixture for describing a human tissue. As a consequence, according to the prior art, only the foreground substance is taken into account.

The dose and quality of X-ray beams has hitherto been optimized to the contrast-to-noise ratio between the foreground substance to be examined and human soft tissue. Particular problems arise in the case of demanding projections. Demanding projections arise when the foreground object to be examined is arranged in front of or behind the background object that consists of an identical or similar background substance to the foreground object. In this case, the second X-ray beam, which passes through the background object and not through the foreground object, passes through the same substance as the first X-ray beam, which passes through both the background object and the foreground object.

These cases may relate to overlapping coils in an aneurysm or bone cement over thick bone, dental fillings, implants in bone structures, or ultrasound probes over the spinal column and are not specially treated according to the current prior art.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a contrast-to-noise ratio in an X-ray capture for various combinations of a foreground substance of a foreground object and a background substance of a background object may be increased. As another example, the contrast-to-noise ratio in the presence of a background substance that is the same as the foreground substance may be increased.

A first aspect of the present embodiments relates to a method for operating an X-ray imaging system.

The present embodiments provide that the X-ray imaging system is operated such that a specified contrast-to-noise ratio of a foreground object in front of a background object is made available in an X-ray capture.

The foreground object includes a foreground substance. The background object includes a background substance. In other words, the present embodiments provide that the X-ray imaging system is to image in an X-ray capture a foreground object that is arranged, in relation to an X-ray beam course, in front of and/or behind the background object. The objective of the method is to achieve the specified contrast-to-noise ratio in the X-ray capture. In other words, the present embodiments provide that an intensity of the foreground object differs from an intensity of the background object such that the specified contrast-to-noise ratio is present. The background substance and/or the foreground substance may be made available to the X-ray imaging system as a function of a user input.

A first act provides that an X-ray source of the X-ray imaging system outputs first X-ray beams onto an X-ray detector for acquisition of a first X-ray capture of the object under examination. The object under examination is, for example, arranged between the X-ray source and the X-ray detector. As a result, the first X-ray beams pass through the object under examination.

In a second act, the X-ray detector acquires an entry dose of the first X-ray beams after passage through the object under examination. In other words, the first X-ray beams output by the X-ray source are acquired by the X-ray detector. The X-ray detector ascertains the entry dose of the first X-ray beams acquired thereby. The entry dose may, for example, be dependent on a signal intensity value of the first X-ray beams in a specified subregion of the first X-ray capture or describe a dose with respect to the entire first X-ray capture. The entry dose may, for example, depend on a depth of the object under examination and/or on substances present in the objects under investigation.

In a third act, the entry dose is made available to a control system of the X-ray imaging system. In other words, the ascertained entry dose is transferred to the control system of the X-ray imaging system in order to enable control of the X-ray imaging system by the control system as a function of the entry dose for creation of a second X-ray capture.

In a fourth act, the control system ascertains a parameter value of at least one parameter for output of the second X-ray beams by the X-ray source for acquisition of the second X-ray capture of the object under examination. In other words, the control system ascertains the parameter value of the at least one parameter. The at least one parameter may relate to the output of the second X-ray beams or characteristics of the second X-ray beams themselves that are output by the X-ray source for capturing the second X-ray capture of the object under examination.

The present embodiments provide that the control system ascertains the parameter value according to a specified ascertainment method as a function of the foreground substance, the background substance, and the entry dose. In other words, the parameter value ascertained by the control system is dependent on the foreground substance, the background substance, and the acquired entry dose.

The parameter value of the at least one parameter is parameterized by the control system according to the specified ascertainment method so as to maximize an expected contrast-to-noise ratio between a first signal intensity value in the second X-ray capture of a first X-ray beam of the second X-ray beams that has passed through the background object in an object under examination, and a second signal intensity value in the second X-ray capture of a second X-ray beam that has passed through the background object and the foreground object. The ascertainment method may, for example, include a simulation carried out by the control system using a model. The simulation may, for example, include a Monte Carlo simulation. In the simulation, parameter values may be varied in substeps. The resultant contrast-to-noise ratio may be ascertained for the respective values.

The value of the parameter may be determined as a parameter value for which the greatest contrast-to-noise ratio has been obtained. The ascertainment may also be carried out multidimensionally, where values of a plurality of the parameters are varied.

The values of the parameters that result in the greatest contrast-to-noise ratio may be determined as the parameter values of the parameters.

In a following act, the control system may set a capture of the second X-ray capture using the parameter value of the at least one parameter.

The present embodiments give rise to the advantage that it is possible to enable an elevated contrast-to-noise ratio for various specified combinations of a foreground substance and a background substance.

One development of the present embodiments provides that the foreground substance and the background substance are the same. In other words, the background object may consist of the same substance as the foreground object, and/or the background object may include the same substance as the foreground object. The present embodiments may, for example, provide that the foreground object relates to an implant arranged in the object under examination that is arranged in front of a background object in the form of another implant. The foreground object and the background object may, for example, both consist of or include titanium.

Due to the same substance being used, it is not possible to set the parameter value of the at least one parameter as a function of a different absorption characteristic of the substances. The development gives rise to the advantage that the contrast-to-noise ratio may be improved even in the case of same substances.

One development of the present embodiments provides that the parameter value of the at least one parameter is ascertained according to the specified ascertainment method as a function of a foreground depth of the foreground object and a background depth of the background object. The foreground depth describes a path length of the second X-ray beam through the foreground object. The background depth describes a path length of the second X-ray beam and the first X-ray beam through the background object. The foreground depth may describe a geometric dimension or a range of values of a geometric dimension of the foreground object that may be specified or ascertained by a measurement. Similarly, the background depth may describe a geometric dimension or a range of values of a geometric dimension of the background object. The foreground depth may, for example, describe a width of a foreground object specified as an implant along a direction from the X-ray source to the X-ray detector. The background object may describe a width of another implant along the direction from the X-ray source to the X-ray detector. The other implant may be arranged behind the foreground object. It may, for example, be desired for an overlap region in which the two implants overlap in the second X-ray capture to differ by different signal intensity values from regions in which only the background object is located. The development gives rise to the advantage that path lengths over which X-ray beams are absorbed by the background object alone or by the background object and the foreground object are taken into account for ascertaining the parameter value.

One development of the present embodiments provides that the specified contrast-to-noise ratio is described by a contrast-to-noise ratio. In other words, the specified contrast describes a difference in a signal amplitude between the foreground object and the background object in the second X-ray capture for a known background noise level. The background noise may, for example, be estimated, ascertained from the first X-ray capture, or specified.

One development of the present embodiments provides that the foreground substance and the background substance are a contrast agent. In other words, volumes enhanced by an identical contrast agent may be described by the foreground object and the background object. The present embodiments may, for example, provide that the foreground object describes a first bloodstream and the background object describes a second bloodstream. The contrast agent may, for example, be or include iodine.

One development of the present embodiments provides that the foreground substance and the background substance are platinum. In other words, the foreground object and the background object in each case consist of platinum or at least include the latter. The foreground object and the background object may, for example, be implants.

One development of the present embodiments provides that the foreground substance and the background substance are iron. In other words, the foreground object and the background object in each case consist of iron or at least include iron. The foreground object and the background object may, for example, be stents.

One development of the present embodiments provides that the specified ascertainment method includes retrieval of the parameter value of the at least one parameter from a database by the control system. In other words, the database is stored in the control system. The database may be structured such that the database assigns the parameter value of the at least one parameter to the foreground substance, the background substance, and the entry dose. The database may, for example, include the parameter values that may be ascertained by a control facility via a Monte Carlo method for respective combinations of background substances, foreground substances, and entry dose.

The parameter value of the at least one parameter may be ascertained according to a specified Monte Carlo method.

A second aspect of the present embodiments relates to a method for generating a database via a control apparatus. The method includes ascertaining an entry dose for an object under examination in a specified simulation method.

The object under examination used in the simulation method includes a foreground object made of a foreground substance and a background object made of a background substance. The entry dose is ascertained for first X-rays that pass through the object under examination.

A second act includes ascertaining respective first signal intensity values for a first X-ray beam course of second X-rays through the background object made of the background substance for respective parameter values of the at least one parameter of the second X-rays.

A third act includes ascertaining respective second signal intensity values for the second X-ray beam course of the second X-rays through the background object made of the background substance and a foreground object made of a foreground substance for the respective parameter values of the parameter of the second X-rays.

A fourth act includes ascertaining a parameter value of the at least one parameter, for which a contrast-to-noise ratio relating to a difference between the first signal intensity value and the second signal intensity value has the greatest value for a respective entry dose.

A fifth act includes generating a database that assigns the parameter value to the parameter as a function of the foreground substance, the background substance, and the signal intensity value.

The database may be made available to a control system of an X-ray imaging system.

For application cases or application situations that may arise during the methods and are not described explicitly here, provision may be made according to the methods for an error message and/or a request to submit user feedback to be output and/or a default setting and/or a predetermined initial state to be set.

A third aspect of the present embodiments relates to a control system (e.g., including one or more processors). The control system is configured to ascertain a parameter value of at least one parameter for output of second X-ray beams by an X-ray source for acquisition of a second X-ray capture of an object under examination and to set the parameter value of the at least one parameter in the X-ray apparatus. The present embodiments provide that the control system is configured to ascertain the parameter value according to a specified ascertainment method as a function of a foreground substance, a background substance, and an entry dose.

The ascertainment method is configured to parametrize the parameter value of the at least one parameter so as to maximize an expected contrast-to-noise ratio between a first signal intensity value in the second X-ray capture of a first X-ray beam of the second X-ray beams that has passed through the background object in the object under examination, and a second signal intensity value in the second X-ray capture of a second X-ray beam that has passed through the background object and the foreground object in the object under examination.

The control system may include at least one computing unit.

A fourth aspect relates to an X-ray imaging system.

The X-ray imaging system has an X-ray source that is configured to output first X-ray beams onto an X-ray detector for acquisition of a first X-ray capture of an object under examination. The object under examination is arranged between the X-ray source and the X-ray detector such that the first X-ray beams pass through the object.

The X-ray imaging system is configured to ascertain, via the X-ray detector, an entry dose of the first X-ray beams after passage through the object under examination and to make the entry dose available to a control system of the X-ray imaging system.

The X-ray imaging system is configured to ascertain, according to a specified ascertainment method, a parameter value of at least one parameter for output of second X-ray beams by the X-ray source for acquisition of a second X-ray capture of the object under examination by the control system. The ascertainment method is configured to parametrize the parameter value of the at least one parameter so as to maximize an expected contrast-to-noise ratio between a first signal intensity value in the second X-ray capture of a first X-ray beam of the second X-ray beams that has passed through the background object in the object under examination, and a second signal intensity value in the second X-ray capture of a second X-ray beam that has passed through the background object and the foreground object in the object under examination.

The advantages and developments set out above in connection with the method according to the present embodiments according to the first aspect also apply mutatis mutandis to the control device according to the present embodiments, and the X-ray imaging system according to the present embodiments. The method features shown for the control system and the X-ray imaging system may accordingly be viewed as functional features of corresponding means.

A fifth aspect of the present embodiments relates to a control facility (e.g., including a processor). The control facility is configured to ascertain an entry dose for first X-rays for an object under examination comprising a foreground object made of a foreground substance and a background object made of a background substance.

The control facility is configured to ascertain respective first signal intensity values for a first X-ray beam course of an X-ray beam of second X-rays through a background object made of a background substance for respective parameter values of a parameter of second X-rays.

The control facility is configured to ascertain respective second signal intensity values for a second X-ray beam course of the second X-rays through the background object made of the background substance and a foreground object made of a foreground substance for the respective values of the parameter of the second X-rays.

The control facility is configured to ascertain, as the parameter value of the parameter, the value for which a contrast-to-noise ratio describing a difference between the first signal intensity value and the second signal intensity value has the greatest value for a respective entry dose.

The control facility is configured to generate a database. The database assigns the parameter value of the at least one parameter to the parameter as a function of the foreground substance, the background substance, and the signal intensity value.

The control facility may include at least one computing unit (e.g., having a processor).

The advantages and developments set out above in connection with the method according to the present embodiments according to the second aspect also apply mutatis mutandis to the control facility according to the present embodiments. The method features shown in the control facility may accordingly be viewed as functional features of corresponding means.

In one embodiment, a computer program that is directly loadable into a memory of a control system of an X-ray imaging system, with program means for carrying out the acts of the above-stated method according to the first aspect of the present embodiments when the program is executed in the control system of the X-ray imaging system is provided.

An electronically readable data storage medium (e.g., a non-transitory computer-readable storage medium) with electronically readable control information stored thereon may likewise be present. The electronically readable control information includes at least one described computer program (e.g., product) and is configured such that, when the data storage medium is used in a control system of an X-ray imaging system, the computer program carries out the described method according to the first aspect of the present embodiments.

The storage medium may include a memory unit.

A computing unit may, for example, be taken to be a data processing device that contains a processing circuit. The computing unit may thus, for example, process data for carrying out computing operations. These may optionally also include operations for carrying out indexed access to a data structure (e.g., a look-up table (LUT)).

The computing unit may, for example, contain one or more computers, one or more microcontrollers, and/or one or more integrated circuits (e.g., one or more application-specific integrated circuits (ASIC), one or more field-programmable gate-arrays (FPGA), and/or one or more systems on a chip (SoC)). The computing unit may also contain one or more processors (e.g., one or more microprocessors, one or more central processing units (CPU), one or more graphics processing units (GPU), and/or one or more signal processors, such as one or more digital signal processors (DSPs)). The computing unit may also contain a physical or virtual cluster of computers or others of the stated units.

In various example embodiments, the computing unit contains one or more hardware and/or software interfaces and/or one or more memory units.

A memory unit may be configured as a volatile data memory (e.g., as a dynamic random access memory (DRAM) or static random access memory (SRAM)) or as a nonvolatile data memory (e.g., as a read-only memory (ROM), as a programmable read-only memory (PROM), as an erasable programmable read-only memory (EPROM), as an electrically erasable programmable read-only memory (EEPROM), as a flash memory or flash EEPROM, as a ferroelectric random access memory (FRAM), as a magnetoresistive random access memory (MRAM), or as a phase-change random access memory (PCRAM)).

Independent of the grammatical term usage, individuals with male, female, or other gender identities are included within the term.

Further features of the invention are revealed by the claims, the figures, and the description of the figures. The features and combinations of features stated above in the description and the features and combinations of features stated below in the description of the figures and/or shown in the figures may be included in the invention not only in the respectively stated combination but also in other combinations. For example, the invention may also include embodiments and combinations of features that do not include all the features of a claim as originally worded. The invention may also include embodiments and combinations of features that extend beyond or deviate from the combinations of features recited via the back-references in the claims.

BRIEF DESCRIPTION OF THE DRAWINGS

The invention is explained in greater detail below with reference to specific exemplary embodiments and associated schematic drawings. Same or functionally same elements in the figures may be provided with the same reference signs. Descriptions of same or functionally same elements are not necessarily repeated with regard to different figures.

DETAILED DESCRIPTION

Figure 1:
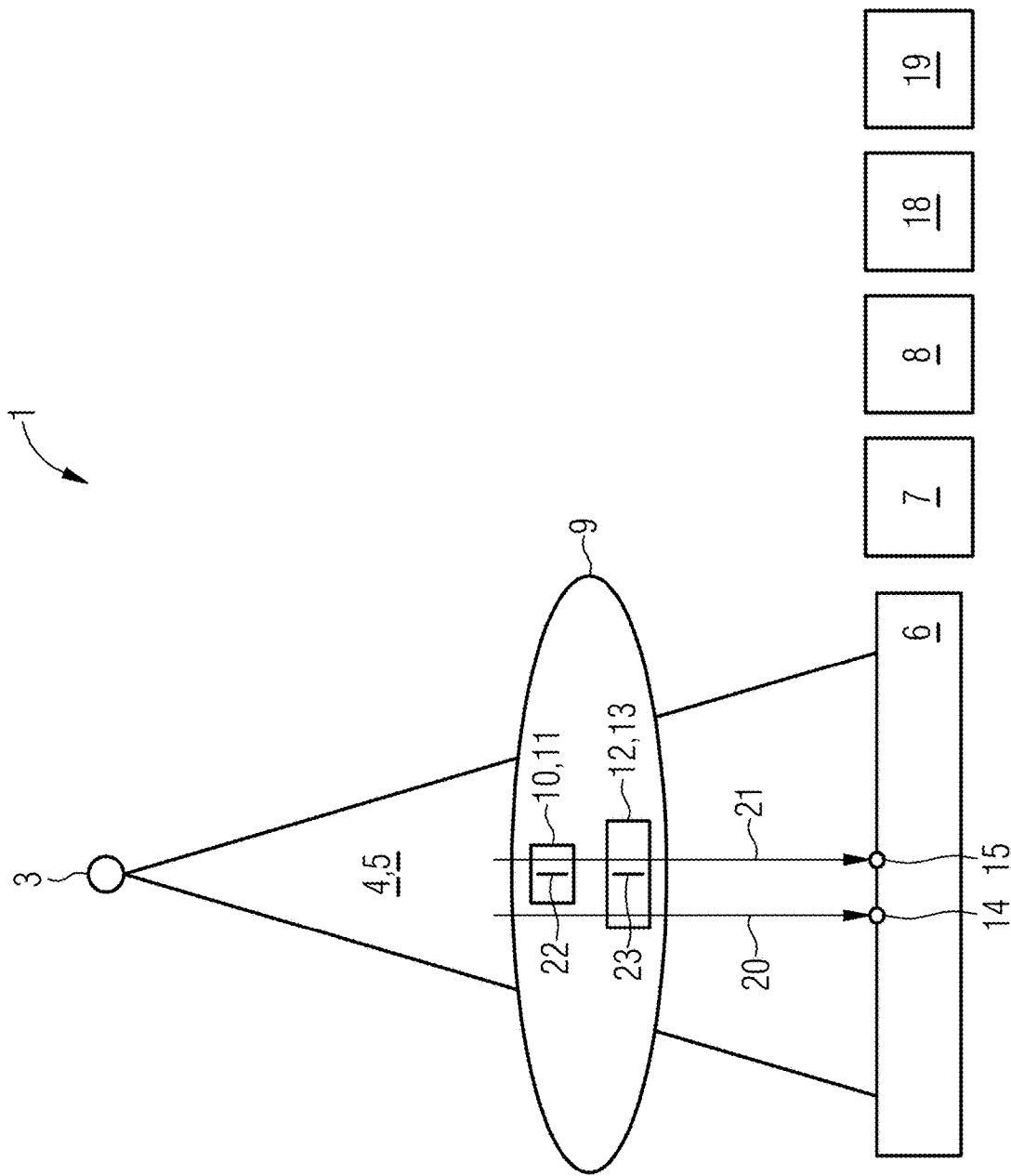
FIG. 1 is a schematic representation of an X-ray imaging system.

FIG. 1 shows a schematic representation of an X-ray imaging system 1.

The X-ray imaging system 1 may include a control system 2 that may be configured to ascertain a parameter value 17 of at least one parameter 16 of the X-ray imaging system 1 for capturing X-ray captures 7, 8 of an object under examination 9 and to set the parameter value in the X-ray imaging system 1. The X-ray imaging system 1 may include an X-ray source 3 that may be configured to output X-rays 4, 5 for capturing the X-ray captures 7, 8 toward an X-ray detector 6 of the X-ray imaging system 1. An object under examination 9 may be arranged between the X-ray source 3 and the X-ray detector 6. The object under examination 9 may include a foreground object 10 made of a foreground substance 11. The object under examination 9 may also include a background object 12 made of a background substance 13.

The foreground object 10 and the background object 12 may be arranged in the object under examination 9 such that, on a path from the X-ray source 3 to the X-ray detector 6, the X-ray beams pass through the foreground object 10 and the background object 12 or only the background object 12.

A first X-ray beam course 20 may describe a path of the X-ray beams 4, 5 through the background object 12.

A second X-ray beam course 21 may describe a path of the X-ray beams 4, 5 through the background object 12 and the foreground object 10.

X-ray beams 4, 5 along the first X-ray beam course 20 may be acquired on the X-ray detector 6 with a first signal intensity value 14. X-ray beams along the second X-ray beam course 21 may have a second signal intensity value 15 on the X-ray detector 6.

Based on a difference between the signal intensity values 14, 15, it is possible to ascertain a contrast-to-noise ratio 19 that describes a measure of a contrast of the foreground object 10, which has the first signal intensity value 14, against the background object 12, which has the second signal intensity value 15, in the X-ray captures 7, 8. To provide better visibility of the foreground object 10 against the background object 12, it may be desired to achieve the greatest possible contrast-to-noise ratio 19. This may be achieved by setting the parameter value 17 of the at least one parameter 16 of the X-ray beams 4, 5. It may be necessary to this end to ascertain the parameter value 17 of the at least one parameter 16 for increasing the contrast-to-noise ratio 19 via the control system 2 and to set the parameter value 17 in the X-ray imaging system 1 for capture of a second X-ray capture 8 via the second X-ray beams 5. The at least one parameter 16 may relate to the output of the second X-ray beams 8 or the second X-ray beams 8 themselves. The parameter 16 may, for example, include an output current, an output voltage, or a pulse length of the second X-ray beams 5.

The signal intensity values 14, 15 may be dependent on an absorption behavior of the objects 10, 12 and the substances 11, 13 thereof. The substances 11, 13 may, for example, have a spectral absorption behavior, where the X-ray beams 4, 5 may be absorbed to a differing extent as a function of a photon energy of the X-ray beams 4, 5.

In order to increase the signal difference, the X-ray imaging system 1 may have the control system 2 that may ascertain the parameter value 17 of the at least one parameter 16 and set the parameter value 17 in the X-ray imaging system 1.

In order to ascertain the parameter value 17 of the at least one parameter 16, the X-ray imaging system 1 may be configured to capture two of the X-ray captures 7, 8 of the object under examination 9 in temporal succession. The control system 2 may be configured to set specified calibration values of the parameters 16 for output of the first X-ray beams 4. The X-ray imaging system 1 may be configured, in order to generate the first X-ray capture 7, by the X-ray source 3 to output the first X-ray beams 4 onto the X-ray detector 6 for acquisition of the first X-ray capture 7 of the object under examination 9. The X-ray detector 6 may be configured to acquire the first X-ray beams 4 and to ascertain an entry dose 18 from the first X-ray capture 7. The entry dose 18 may, for example, describe a signal intensity value within a range of the first X-ray capture 7. The entry dose 18 may, for example, be described as the water value.

The control system 2 may be configured, for the acquired entry dose 18 of the first X-ray capture 7 generated with the first X-ray beams 4, the foreground substance 11 and the background substance 13, to ascertain the at least one parameter value 17 of the at least one parameter 16 for capture of the second X-ray capture 8 via the second X-ray beams 5.

The parameter value 17 of the at least one parameter 16 may be parameterized such that it increases the difference between the first signal intensity value 14 and the second signal intensity value 15 in the second X-ray capture 8 in comparison with the difference in the first X-ray capture 7. It is preferably an optimum value that may result in a maximum difference between the signal intensity values 14, 15. The foreground substance 11 and the background substance 13 may be specified to the control system 2. A foreground depth 22 of the foreground object 10 and a background depth 23 of the background object 12 may likewise be specified to the control system 2. The parameter value 17 of the at least one parameter 16 may consequently also be ascertained as a function of a foreground depth 22 of the foreground object 10 and/or a background depth 23 of the background object 12. The foreground depth 22 and the background depth 23 may describe respective dimensions of the objects 10, 12 that may be acquired or specified. The background depth 23 and the foreground depth 22 may correspond to a path length through that the X-ray beams 4, 5 pass through the respective objects 10, 12 when passing through the object under examination 9.

Further variables of relevance to ascertaining the parameter value 17 of the at least one parameter 16 may include densities of the foreground substance 11 and of the background substance 13.

The control system 2 may be configured to ascertain the parameter value 17 of the at least one parameter 16 according to a specified ascertainment method. The control system 2 may, for example, be configured to carry out simulations using the background substance 13, the foreground substance 11, and the entry dose 18 in order to ascertain the parameter value 17 of the at least one parameter 16. The simulations may, for example, include Monte Carlo simulation.

The present embodiments may provide that a database 25 is made available to the control system 2. The database 25 may, for example, have been created by a control facility 24. The database 25 may output the parameter value 17 of the at least one parameter 16 for the foreground substance 11, the background substance 13, and the entry dose 18.

The control facility 24 may be configured to generate the database 25 via simulations (e.g., via Monte Carlo simulations). First, signal intensity values 14 and second signal intensity values 15, and entry doses 18 for second X-ray beams 5 of various values of the at least one parameter 16 may, for example, be ascertained in the simulations. The foreground substance 11, the background substance 13, and the values of the parameters 16 may be varied in respective individual simulations. The control facility 24 may set up the parameter value 17 of the at least one parameter 16 in the database 25 ascertained for the foreground substance 11, the background substance 13, and the entry dose 18.

The ascertainment method may include retrieval of the parameter value 17 from the database 25 by the control system 2. The advantage of making the database 25 available is that any complex computational and/or simulation method may be carried out in advance by the control facility 24. The duration of ascertainment by the control system 2 may be reduced as a consequence. The database 25 may be stored on a control system 2. The database 25 may be stored on the control facility 24, the control system 2, or a central storage device outside the X-ray imaging system 1 and made accessible to the control system 2 via a network, for example.

Once the parameter value 17 of the at least one parameter 16 has been ascertained, the control system 2 may be configured to set the parameter value 17 of the at least one parameter 16 in the X-ray imaging system 1 and initiate the output of the second X-ray beams by the X-ray source 3 in order for the X-ray imaging system 1 to capture the second X-ray capture 8 of the object under examination 9.

Figure 2:
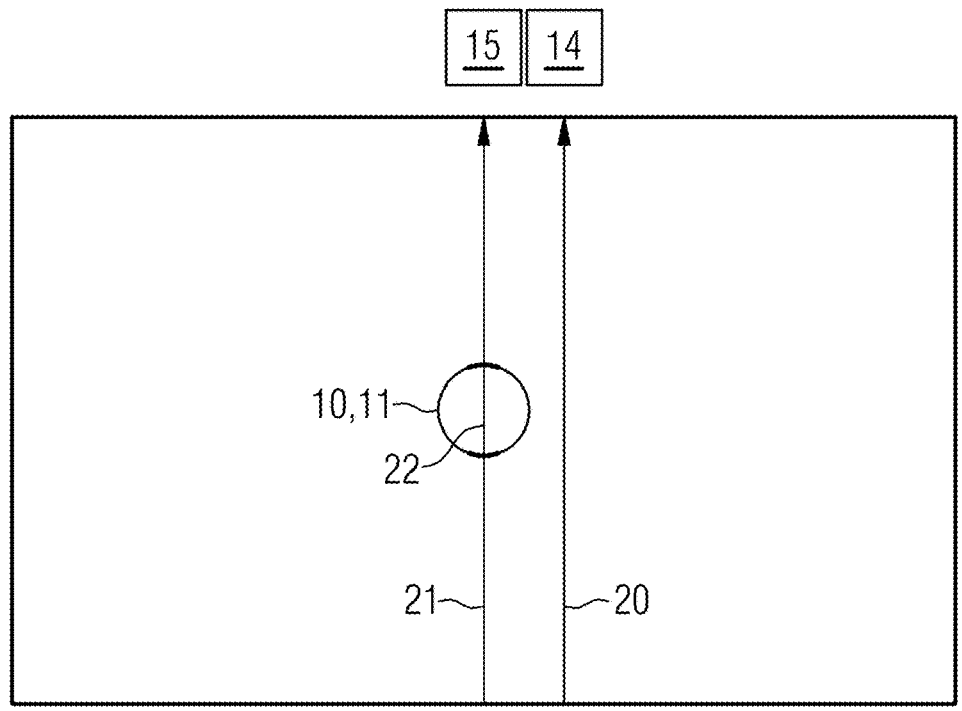
FIG. 2 is a schematic representation of a foreground object.

FIG. 2 shows a schematic representation of a foreground object.

FIG. 2 shows an assumption according to the prior art for ascertaining the parameter value 17. The foreground object 10 (e.g., an implant that includes platinum as the foreground substance 11) is shown. It is assumed that the foreground object 10 is arranged in the background object 12 of soft tissue as the background substance 13. For increasing the contrast-to-noise ratio 19, the parameter value 17 is accordingly ascertained as a function of spectral absorption characteristics of the tissue and the platinum.

Figure 3:
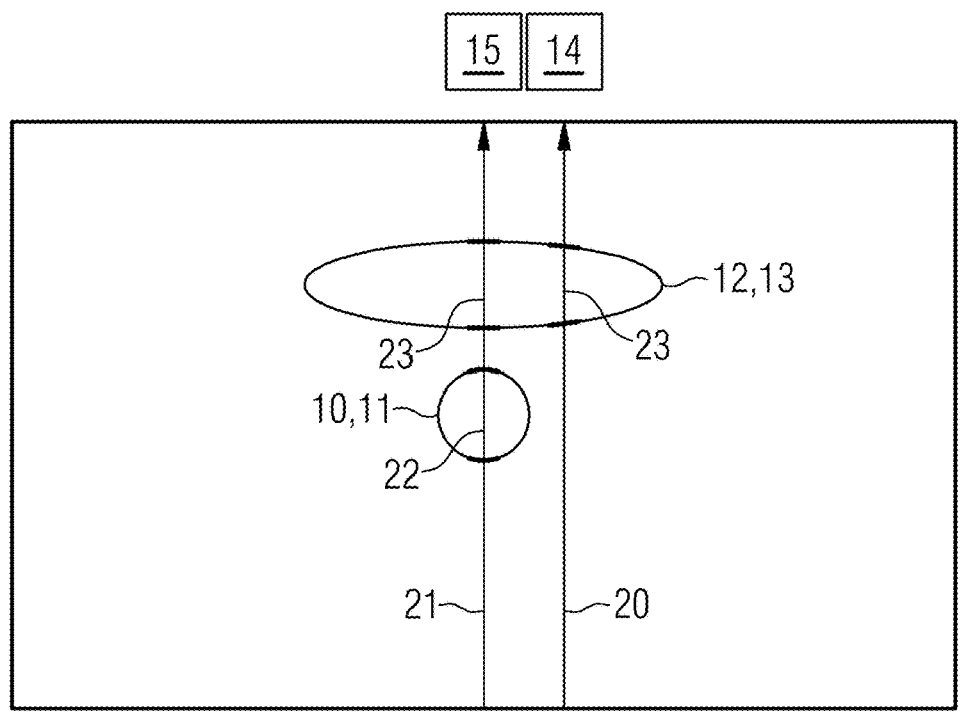
FIG. 3 is a schematic representation of a foreground object and a background object.

FIG. 3 shows a schematic representation of a foreground object and a background object.

FIG. 3 shows the foreground object 10, also shown in FIG. 2, with platinum as the foreground substance 11 in front of the background object 12, which may also include platinum as the background substance 13. Unlike in the case shown in FIG. 2, it is desired to increase the difference between the two objects 10, 12 made of the same substance 11, 13. As a result, visibility of the foreground object 10 made of platinum may be increased when the foreground object 10 is located in front of the background object 12 that is, for example, an already implanted background object 12 made of platinum. This may be a typical case when a coil is added to an already existing coil package.

Figure 4:
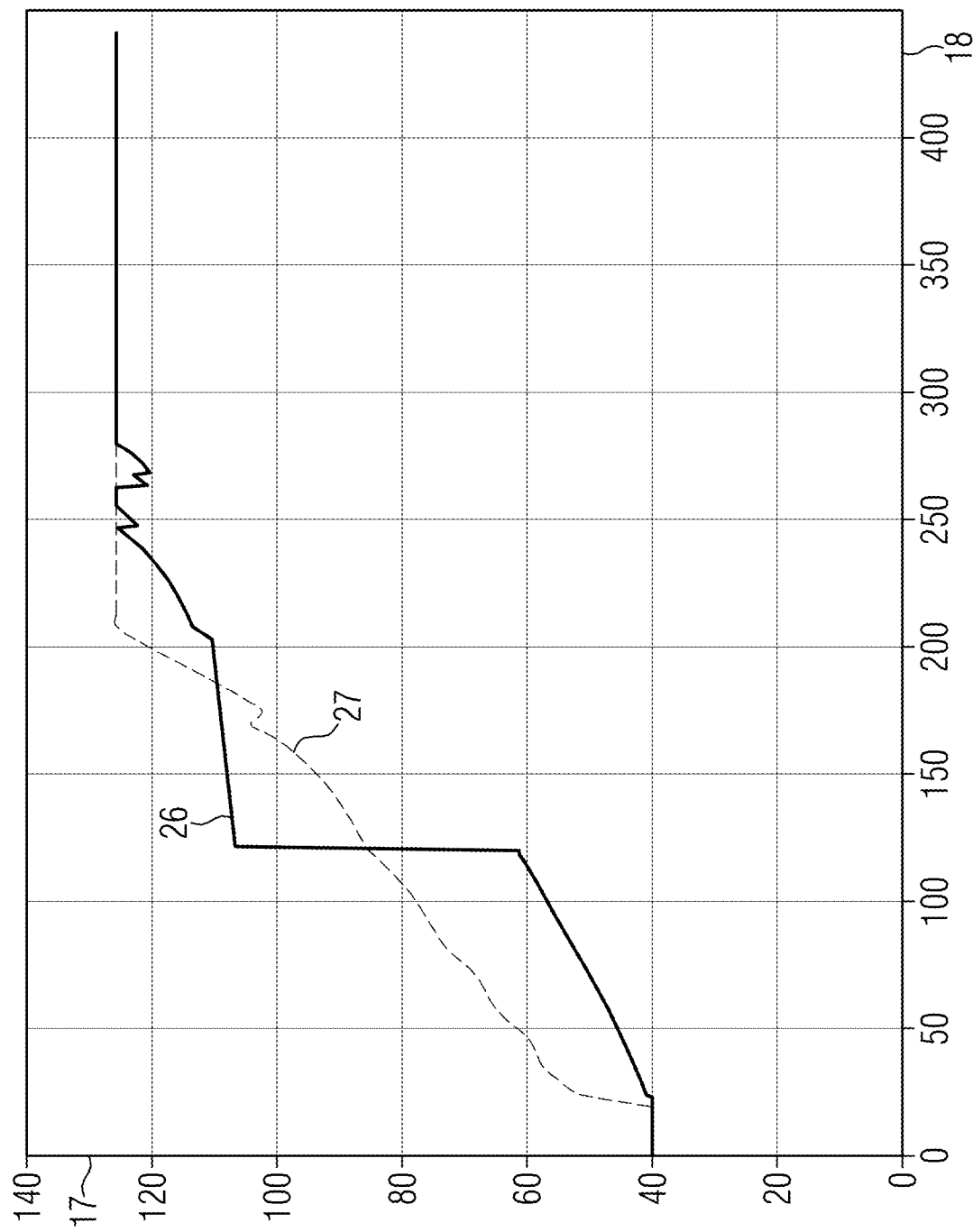
FIG. 4 is a schematic representation of parameter value curves as a function of the entry dose.

FIG. 4 shows a schematic representation of parameter value curves of the parameter value as a function of the entry dose.

The first parameter value curve 26 of the parameter value curves 26, 27 shows the parameter value 17 of the at least one parameter 16 as a function of the entry dose 18 for platinum as the foreground substance 11 and water or tissue as the background substance 13. The first parameter value curve 26 may be assigned to the case shown in FIG. 2. A second parameter value curve 27 shows the parameter value 17 of the at least one parameter 16 as a function of the entry dose 18 for platinum as the foreground substance 11 and platinum as the background substance 13. The second of the curves may be assigned to the case shown in FIG. 3. The parameter 16 may be described by the optimum acceleration voltage of the X-ray source 3 in kV, and the entry dose 18 the water value in mm.

In the case of the first parameter value curve 26, the foreground substance 11 and the background substance 13 differ from one another. In the case of the second parameter value curve 27, the foreground substance 11 and the background substance 13 are the same.

The first parameter value curve 26 shows a large jump discontinuity. This is caused by the K-edge of platinum at 78 keV, from which absorption then again gets substantially better and where the platinum may again stand out relative to the background substance 13.

If the background object 12 also consists of platinum, the foreground substance 11 and the background substance have the same spectral absorption characteristics. In other words, it is no longer possible to gain any advantage from the K-edge of the platinum for increasing the difference and the ascertained parameter value 17 of the acceleration voltage only runs constantly further upward when the water value increases.

Figure 5:
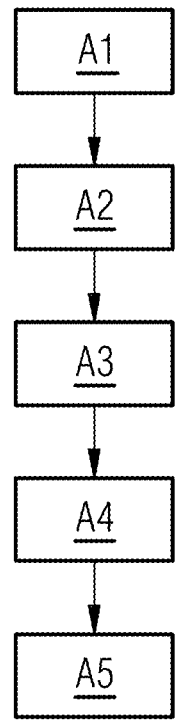
FIG. 5 is a schematic representation of a method for generating a database via a control apparatus.

FIG. 5 shows a schematic representation of a method for generating a database via a control apparatus.

Act A1 includes ascertaining an entry dose 18 for an object under examination 9 including a foreground object 10 made of a foreground substance 11 and a background object 12 made of a background substance 13 for first X-rays 4.

Step A2 includes ascertaining respective first signal intensity values 14 for a first X-ray beam course 20 of one of the second X-ray beams through a background object 12 made of a background substance 13 for respective values of a parameter 16 of the second X-ray beams 5.

Act A3 includes ascertaining respective second signal intensity values 15 for a second X-ray beam course 21 of one of the second X-ray beams through the background object 12 made of the background substance 13 and a foreground object 10 made of a foreground substance 11 for the respective values of the parameter 16 of the second X-ray beams 5.

Act A4 includes ascertaining the value of the parameter 16 for which a difference between the first signal intensity value 14 and the second signal intensity value 15 has the greatest value for a respective entry dose 18. The ascertained value is then determined as the parameter value 17.

Act A5 includes generating a database 25. The database 25 assigns the parameter value 17 to the parameter 16 as a function of the foreground substance 11, the background substance 13, and the entry dose 18.

Figure 6:
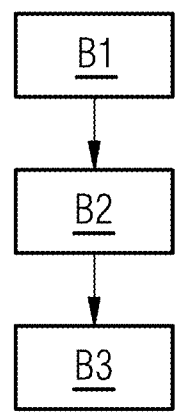
FIG. 6 is a schematic representation of a method for operating an X-ray imaging system.

FIG. 6 shows a schematic representation of a method for operating an X-ray imaging system 1.

Act B1 includes outputting first X-ray beams onto an X-ray detector 6 via an X-ray source 3 for acquisition of a first X-ray capture 7 of the object under examination 9. The object under examination 9 is arranged between the X-ray source 3 and the X-ray detector 6 and is passed through by the first X-ray beams.

Act B2 includes acquiring, by the X-ray detector 6, an entry dose 18 of the first X-ray beams after passage through the object under examination 9. Act B2 further includes making the entry dose 18 available to a control system 2 of the X-ray imaging system 1.

Act B3 includes ascertaining a parameter value 17 of at least one parameter 16 for output of second X-ray beams by the X-ray source 3 for acquisition of a second X-ray capture 8 of the object under examination 9 by the control system 2. The parameter value 17 is ascertained by the control system 2 according to a specified ascertainment method as a function of the foreground substance 11, the background substance 13, and the entry dose 18. The parameter value 17 increases a contrast-to-noise ratio 19 contrast enhancement of the foreground object 10 from the background object 12 in the second X-ray capture 8.

Before image processing may further optimize the visibility of a specific contrast, it is important to optimize the corresponding contrast-to-noise ratio by suitably setting the physical parameters such as voltage, current, filtering, and pulse width. The X-ray captures are the input data for image processing and are to have an optimum contrast-to-noise ratio for the contrast in question.

The problem of demanding projections may be solved by optimizing the physical dose control parameters for the contrast-to-noise ratio of the respective contrast to be enhanced. This generalizes the concept of contrast-to-noise-ratio for contrast in front of a human soft tissue background.

If coils in aneurysms are projected one on top of the other, the aim may be to improve the contrast of coil overlaps in comparison to individual coils. In this situation, it is advantageous to optimize for platinum against platinum as the background substance as the relevant contrast, instead of projecting platinum onto human soft tissue.

Via simulations (e.g., via Monte Carlo simulations), it is possible to identify the optimum parametrization of a physical image chain that generates X-ray beams for a desired visual contrast. In the case of demanding projections, the background substance soft human tissue may be replaced by other materials. The results of simulations (e.g., Monte Carlo simulations) may be stored in a database that may be accessed in real time.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating an X-ray imaging system, the method comprising:
   outputting first X-ray beams onto an X-ray detector by an X-ray source for acquisition of a first X-ray capture of an object under examination, wherein the object under examination is arranged between the X-ray source and the X-ray detector and is passed through by the first X-ray beams;
   acquiring, by the X-ray detector, an entry dose of the first X-ray beams after passage through the object under examination;
   ascertaining, by a control system of the X-ray imaging system, a parameter value of at least one parameter for output of second X-ray beams by the X-ray source for acquisition of a second X-ray capture of the object under examination,
   wherein the parameter value is ascertained by the control system according to a specified ascertainment method as a function of a foreground substance of a foreground object arranged in the object under examination, a background substance of a background object arranged in the object under examination, and the entry dose, and
   wherein the ascertainment method parameterizes the parameter value of the at least one parameter, such that an expected contrast-to-noise ratio between a first signal intensity value in the second X-ray capture of a first X-ray beam course of the second X-ray beams that has passed through the background object in the object under examination, and a second signal intensity value in the second X-ray capture of a second X-ray beam course that has passed through the background object and the foreground object is maximized.

2. The method of claim 1, wherein the foreground substance and the background substance are identical.

3. The method of claim 1, wherein the parameter value of the at least one parameter is ascertained according to the specified ascertainment method as a function of a foreground depth of the foreground object and a background depth of the background object, and wherein the foreground depth describes a path length of the second X-ray beam course through the foreground object, and the background depth describes a path length of the second X-ray beam course and the first X-ray beam course through the background object.

4. The method of claim 1, wherein the expected contrast-to-noise ratio is described by a contrast-to-noise ratio.

5. The method of claim 1, wherein the foreground substance and the background substance are a contrast agent.

6. The method of claim 1, wherein the foreground substance and the background substance are platinum.

7. The method of claim 1, wherein the foreground substance and the background substance are iron.

8. The method of claim 1, wherein the specified ascertainment method comprises retrieval of the parameter value of the at least one parameter from a database by the control system.

9. The method of claim 1, wherein the parameter value of the at least one parameter is ascertained by the control system according to a specified Monte Carlo method.

10. A method for generating a database, the method being carried out by a control facility in a specified simulation method and comprising:
    ascertaining an entry dose for an object under examination, comprising a foreground object made of a foreground substance and a background object made of a background substance, for first X-ray beams;
    ascertaining respective first signal intensity values for a first X-ray beam course through the background object made of the background substance for respective parameter values of a parameter of second X-ray beams;
    ascertaining respective second signal intensity values for a second X-ray beam course of an X-ray beam through the background object made of the background substance and the foreground object made of the foreground substance for the respective parameter values of the parameter of the second X-ray beams;
    ascertaining the parameter value for which a contrast-to-noise ratio describing a difference between the first signal intensity value and the second signal intensity value has a greatest value for the respective entry dose; and
    generating a database, wherein the database assigns the parameter value to the parameter as a function of the foreground substance, the background substance, and the entry dose.

11. An X-ray imaging system comprising:
    an X-ray source and an X-ray detector, wherein the X-ray source is configured to output first X-ray beams onto the X-ray detector for acquisition of a first X-ray capture of an object under examination, wherein the object under examination is arranged between the X-ray source and the X-ray detector and is passed through by the first X-ray beams, wherein the X-ray detector is configured to acquire an entry dose of the first X-ray beams after passage through the object under examination; and
    a control system configured to:
      receive the entry dose;
      ascertain a parameter value of at least one parameter for output of second X-ray beams by the X-ray source for acquisition of a second X-ray capture of the object under examination; and ascertain the parameter value as a function of a foreground substance, a background substance, and the entry dose according to the specified ascertainment method, wherein the ascertainment method parameterizes the parameter value of the at least one parameter so as to maximize an expected contrast-to-noise ratio between a first signal intensity value in the second X-ray capture of a first X-ray beam of the second X-ray beams that has passed through the background object in an object under examination, and a second signal intensity value in the second X-ray capture of a second X-ray beam that has passed through the background object and the foreground object.

\* \* \* \* \*